United States Patent [19]
Criton et al.

[11] Patent Number: 6,036,643
[45] Date of Patent: Mar. 14, 2000

[54] ULTRASONIC HARMONIC DOPPLER IMAGING

[75] Inventors: Aline Laure Criton, Seattle; Marshall Taylor Robinson, Snohomish; Thanasis Loupas, Seattle; Roy Beck Peterson, Redmond; Patrick Rene' Pesque, Bothell; Helen Frances Routh, Seattle, all of Wash.

[73] Assignee: Advanced Technology Laboratories, Inc., Bothell, Wash.

[21] Appl. No.: 09/079,139

[22] Filed: May 14, 1998

[51] Int. Cl.[7] .................................................. A61B 8/00
[52] U.S. Cl. ........................... 600/454; 600/455; 600/443
[58] Field of Search ..................................... 600/441, 442, 600/443, 458, 447, 453, 440, 553, 455, 454; 364/485

[56] References Cited

U.S. PATENT DOCUMENTS

| | | |
|---|---|---|
| 4,714,846 | 12/1987 | Pesque . |
| 5,177,691 | 1/1993 | Welles et al. ............................ 364/485 |
| 5,285,788 | 2/1994 | Arenson et al. . |
| 5,410,516 | 4/1995 | Uhlendorf et al. . |
| 5,435,311 | 7/1995 | Umemura . |
| 5,608,690 | 3/1997 | Hossack et al. . |
| 5,718,229 | 2/1998 | Pesque et al. ........................... 600/441 |
| 5,740,128 | 4/1998 | Hossack et al. . |
| 5,833,613 | 11/1998 | Averkiou et al. ........................ 600/440 |
| 5,860,924 | 1/1999 | Quistgaard .............................. 600/441 |
| 5,879,303 | 3/1999 | Averkiou et al. . |
| 5,882,315 | 3/1999 | Ji et al. ................................... 600/553 |
| 5,897,500 | 4/1999 | Zhao . |
| 5,924,991 | 7/1999 | Hossack et al. . |
| 5,928,151 | 7/1999 | Hossack et al. . |

FOREIGN PATENT DOCUMENTS

| | | |
|---|---|---|
| WO 98/20361 | 5/1998 | WIPO . |
| WO 98/57583 | 12/1998 | WIPO . |

OTHER PUBLICATIONS

Starritt, Evidence for ultrasonic finite amplitude distortion in muscles using medical equipment, JASA 77(1), Jan. 1985 at 302–06.

Muir, Prediction of nonlinear acoustic effects at biomedical frequencies and intensities, Ult. in Med. & Biol, vol. 6 at 345–57 (1980).

Starritt, The development of harmonic distortion in pulsed finite–amplitude ultrasound passing through liver, Phys. Med. Biol. vol. 31, no. 12, 1401–09 (1986).

Ward, Non–linear propagation applied to the improvemenet of lateral resolution in medical ultrasound scanners, 1995 World Cong. on Ult. at 965–68.

Simpson, Pulse Inversion Doppler: A New Method for Detecting Nonlinear Echoes From Microbubble Contrast Agents (Oct. 1997).

Muir, Nonlinear Effects in Acoustic Imaging, Acoustical Imaging, vol. 9 at 93–109 (Plenum Press, NYC, 1980).

Christopher, Finite Amplitude Distortion–Based Inhomogenous Pulse Echo Ultrasonic Imaging, IEEE Trans. Ultr., Ferro. & Freq. Contr., vol. 44, Jan. 1997 at 123.

Burns et al., Harmonic Power Mode Doppler Using Microbubble Contrast Agents, J.E.M.U. vol. 16. No. 4 at 132–42 (Massou, Paris, 1995).

(List continued on next page.)

*Primary Examiner*—Jeffrey R. Jastrzab
*Assistant Examiner*—Maulin Patel
*Attorney, Agent, or Firm*—W. Brinton Yorks, Jr.

[57] ABSTRACT

An ultrasonic diagnostic imaging system and method are described by which a fundamental frequency signal is transmitted into the body and harmonic (nonlinear) echo returns are received from the transmission. The harmonic echo signals are Doppler processed and displayed. The harmonic Doppler signals may be displayed alone, or in combination with a fundamental frequency or harmonic grayscale image. In a preferred embodiment harmonic signals returned from moving tissue are segmented on an intensity or frequency basis and displayed. The inventive apparatus and method provide highly resolved ultrasonic images of moving tissue which are substantially unobscured by image clutter from structures or tissue in the near field.

36 Claims, 3 Drawing Sheets

OTHER PUBLICATIONS

Burns, Harmonic Imaging with Ultrasound Contrast Agents, Clin. Radiology, vol. 51, Suppl. 1, at 50–55 (Great Britain 1996).

Burns et al., Harmonic Imaging Principles and Preliminary Results, Angiology, vol. 47, No. 7 Part 2 at 563–574 (Jul. 1996, New York).

Burns, Presentation of Papers Nos. 241, 243, 1046, 1438, 1682, 166 Supplements to Radiology (Nov. 1992 vol. 185, Nov. 1993 vol. 189, Nov. 1994 vol. 193, Nov. 1995 vol. 197, Nov. 1996 vol. 201).

Ward et al., Nonlinear propagation applied to the improvement of resolution in diagnostic medical ultrasound, Acoust. Soc. Am. 101(1) at 143–54 (Jan. 1997).

Schrope et al., Second Harmonic Ultrasonic Blood Perfusion Measurement, Ult. in Med & Biol. 19(7) at 567–79 (Pergamon Press 1993).

ULTRASONIC HARMONIC DOPPLER IMAGING

This invention relates to the noninvasive imaging of moving tissue and fluids inside the body, and in particular to the ultrasonic imaging of bloodflow and moving tissue through the Doppler processing of the nonlinear response to transmitted ultrasonic waves.

As ultrasonic waves are transmitted into and pass through the body their interaction with the body gives rise to the development of nonlinearities in the signals. These nonlinear signal components including harmonic frequencies of the fundamental transmit frequency can be reflected from tissue and blood cells in the same manner as fundamental frequency signals, and the reflections can be detected and used to form an ultrasonic image. As explained in U.S. Pat. No. 5,879,303 entitled "Ultrasonic Diagnostic Imaging of Response Frequency Differing From Transmit Frequency" there are a number of characteristics of nonlinear signal components which may be used to good advantage in imaging. Among these are the reduced sidelobe level of the nonlinear or harmonic beam and the fact that the nonlinear signal components are not transmitted but arise during passage through the body.

The present inventors have discovered further aspects of these nonlinear or harmonic echo signals which can produce highly desirable results in certain clinical imaging applications. The present inventors have discovered that harmonic echo signals, despite the fact that they are effectively distortions of the transmitted signal, can be Doppler processed to yield Doppler shifted signals representing frequency shift, velocity, Doppler power, and variance.

Seemingly inhibiting this discovery are two laws of physics which affect harmonic signals. One is that the amplitude, or intensity, of a harmonic signal is less than that of the fundamental signal, giving harmonic signals a lesser signal to noise characteristic than that of the fundamental frequency signal. The other is that ultrasonic waves undergo depth dependent frequency attenuation as they pass through the body. Since harmonic frequency signals are at multiples of the fundamental transmit frequency, they are subject to these principles and tend to arise at lower amplitudes and become more rapidly attenuated by passage through the body than lower fundamental frequencies. This would seem to limit the ability to measure bloodflow characteristics at deeper depths inside the body through the Doppler use of harmonic frequencies.

In accordance with the principles of the present invention, the present inventors have discovered that Doppler processed harmonic signals can be advantageously used to measure and display bloodflow in certain areas of the body such as the coronary arteries, and tissue motion inside the body such as the moving walls of the beating heart. Bloodflow in the left ventricular coronary arteries is well suited to harmonic imaging since the proximity of these coronary arteries to the surface of the body enables the reception of acceptably diagnostic harmonic Doppler signals. The stronger harmonic reflections from tissue are at initial intensity levels which prolong their detectability even after lengthy passage through the body as compared to the usual Doppler returns from bloodflow. The higher level Doppler harmonic signals from tissue also facilitate the segmentation of heart wall tissue from chamber bloodflow, enabling more precise visualization of the heart wall. The development of the nonlinear components only after passage through tissue reduces clutter from the ribs which is problematic in transthoracic cardiac imaging. The clutter due to changes in the speed of sound as fundamental waves pass through fatty tissue is also greatly reduced by the use of Doppler processed harmonic signals.

Figure 1:
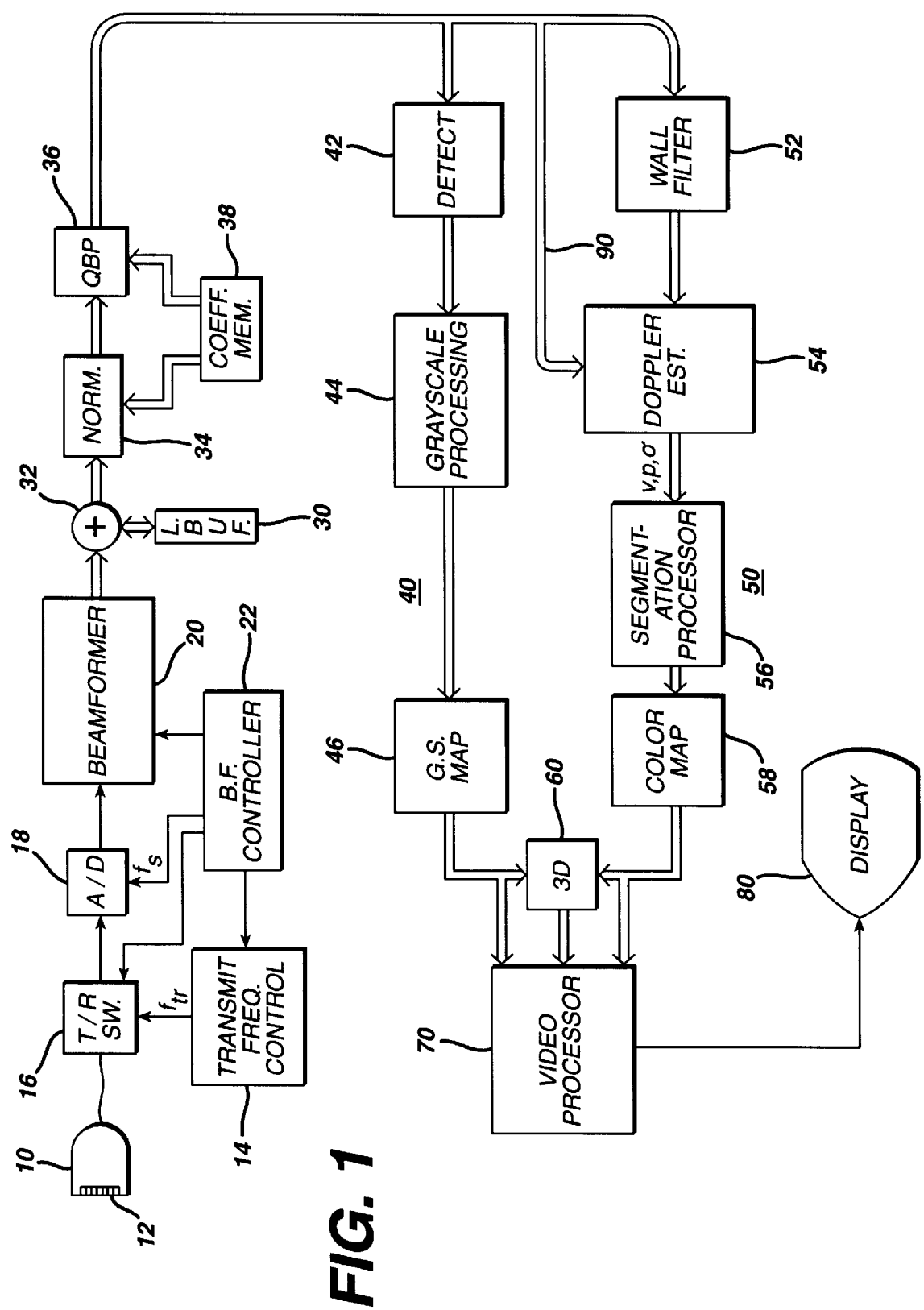
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A probe or scanhead 10 includes a transducer array 12 which transmits ultrasonic waves in a range of frequencies including a fundamental frequency $f_{tr}$ into the body and receives echoes returned from blood cells and tissue inside the body. The transmit frequency $f_{tr}$ and the timing of ultrasonic wave transmission is under the control of a transmit frequency controller 14. The transmit waveforms and received echo signals are coupled to and from the transducer array by a transmit/receive switch 16. The T/R switch 16 couples received echo signals to an analog to digital (A/D) converter 18 which converts the received echo signals into digital signal samples by sampling the received signals at a sampling frequency $f_s$ appropriate for the bandwidth of the received signals. The digital signals are coupled to a beamformer 20 to form digital coherent echo signals. The operation of the transmit frequency controller, the T/R switch, the A/D converter, and the beamformer is coordinated by a beamformer controller 22.

The coherent echo signals are coupled by way of an adder 32 to a normalizing circuit 34. Also coupled to the adder 32 is a line buffer 30. The line buffer and adder are used to separate the harmonic signal components of the received echo signals by the pulse inversion technique as discussed more fully below. The normalizing circuit uses a digital multiplier to vary the gain of the received signals by a sequence of coefficients to compensate for a dynamically varying transducer aperture as echoes are received from increasing depths. The output of the normalizing circuit 34 is coupled to the input of a quadrature bandpass filter (QBP) 36. The quadrature bandpass filter provides three functions: band limiting the RF echo data, producing in-phase and quadrature pairs of scanline data, and digitally demodulating echo signals to an intermediate or baseband range of frequencies. The QBP comprises two separate filters, one producing in-phase samples (I) and the other producing quadrature samples (Q), with each filter being formed by a plurality of multiplier-accumulators (MACs) implementing an FIR or an IIR filter. The characteristics of the normalizing circuit and the QBP are determined by coefficients provided by a coefficient memory 38.

The harmonic echo signals are coupled to a B mode processor 40 and to a Doppler processor 50. In the B mode processor 40 the harmonic echo signals are detected by a square law detector 42 of the form $\sqrt{I^2+Q^2}$. The detected grayscale signals then undergo grayscale processing at 44 such as log compression and other dynamic range and noise level adjustments. The grayscale signals are mapped to the desired display range and image format by a grayscale mapping circuit 46.

In accordance with the principles of the present invention, the harmonic (nonlinear) echo signals are Doppler processed to obtain Doppler shift characteristics such as frequency (velocity), Doppler power (intensity), acceleration or variance. The Doppler processor 50 will process an ensemble of two or more received harmonic echo sequences from the same spatial location and determine the Doppler phase or frequency shift. The Doppler processor may estimate the Doppler shift by a fast Fourier transform (FFT) or autocorrelation estimator 54. The estimator 54 may also comprise a moving target indicator as described in U.S. Pat. No. 5,718,229. Preferably the Doppler estimator employs two dimensional autocorrelation which performs autocorrelation in both time and space, as described in U.S. Pat. No. 5,386,830. Two dimensional autocorrelation has been found to produce precise, highly resolved Doppler shift estimates. The Doppler estimator operates using a harmonic reference frequency in the range of $2f_{tr}$ in the Doppler equation. That is, a Doppler equation of the form $$\Delta f = \frac{2v f_o \cos \theta}{c}$$

is used, where $f_0 = 2f_{tr}$

The harmonic echo signals are coupled to the Doppler estimator 54 by two paths, a bus 90 or by way of a wall filter 52. The wall filter 52 removes low frequency tissue signal components from the broadband harmonic echo signals when the user only desires to process and display bloodflow information. When the user desires to image moving tissue or both moving tissue and bloodflow, the wall filter is bypassed and Doppler estimation is done using the unfiltered harmonic signals on bus 90.

Figure 2:
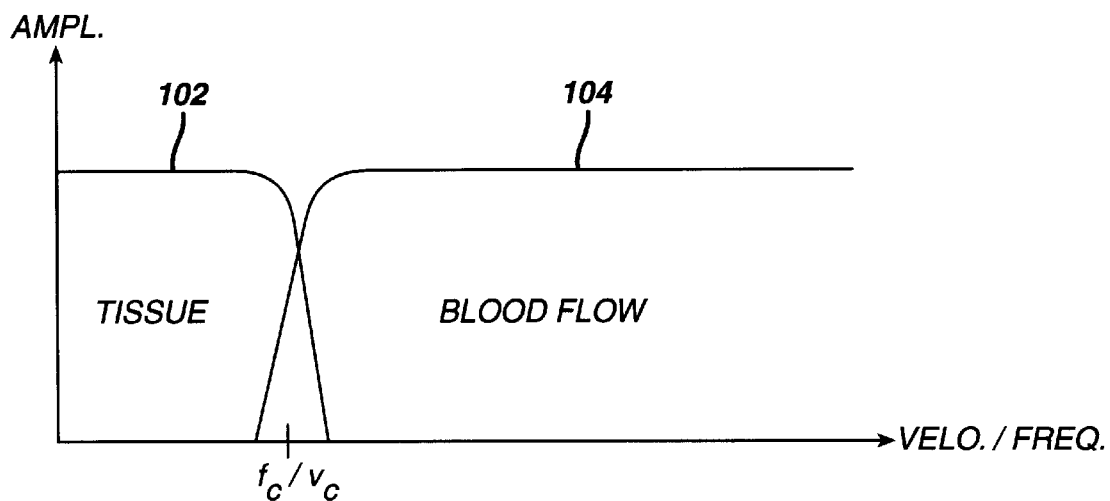
FIG. 2 illustrates the frequency bands of tissue and bloodflow Doppler signals.

The operation of the wall filter 52 is illustrated by the passbands of FIG. 2, which are drawn to the velocity/frequency scale of the Doppler estimator 54. The right passband 104 is a high frequency passband above a cutoff frequency or velocity ($f_c/v_c$) of 50 Hz to 500 Hz, above which the Doppler frequencies generally correspond to bloodflow velocities. For harmonic colorflow imaging, the wall filter will be employed to eliminate signals below this bloodflow signal passband 104 which, in the colorflow imaging of bloodflow, would be regarded as clutter. For harmonic Doppler tissue imaging the wall filter 52 is bypassed to Doppler process all received signals, those emanating from both tissue and blood cells. The echoes returning from tissue would generally be found in the lower frequency passband 102 below the 50–500 Hz cutoff.

Figure 3:
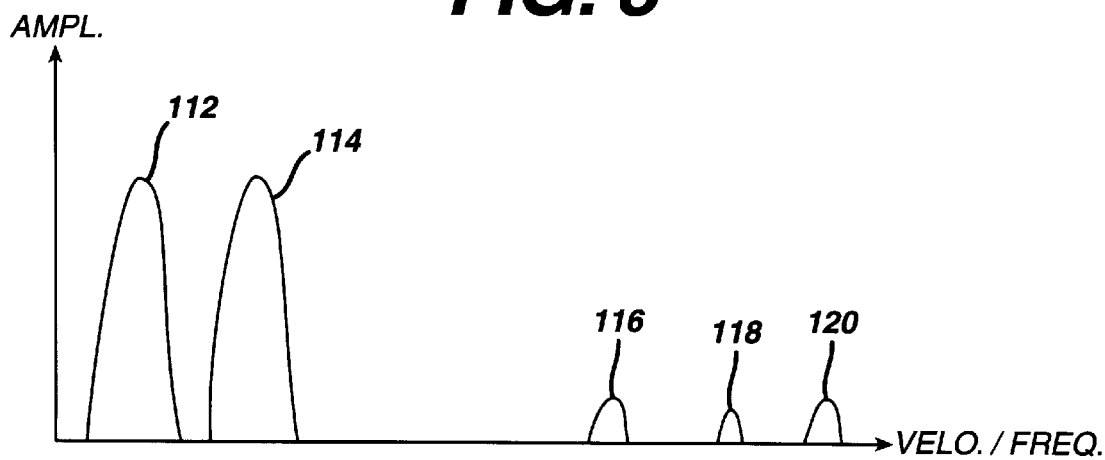
FIG. 3 illustrates the relative amplitudes of tissue and bloodflow Doppler signals.
Figure 4:
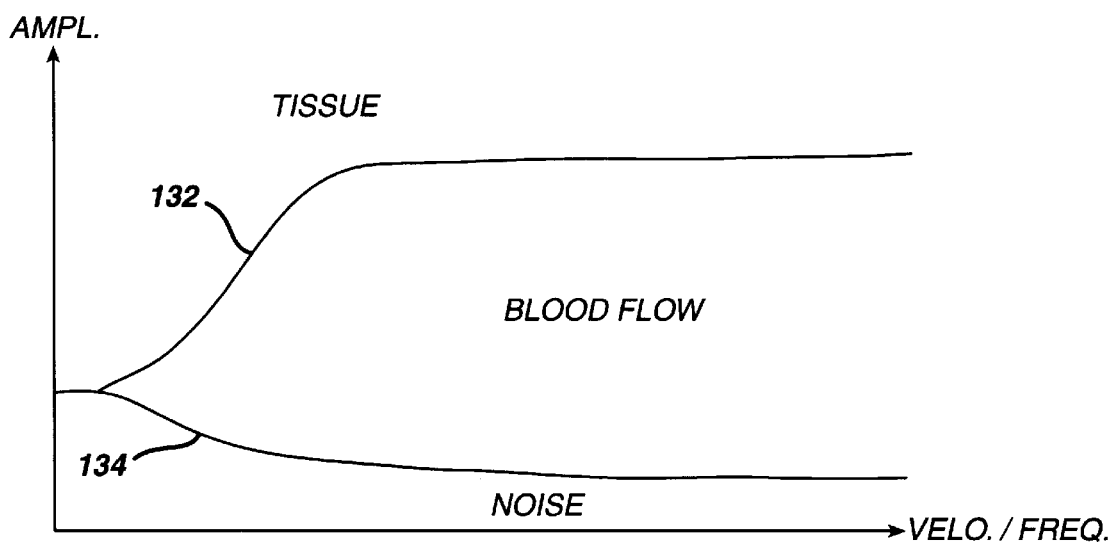
FIG. 4 illustrates the multivariate segmentation of harmonic Doppler tissue and bloodflow signals.

In accordance with a further aspect of the present invention, a segmentation processor 56 is employed following the Doppler estimator 54 when it is desired to segment only harmonic tissue motion or harmonic bloodflow information. The segmentation processor operates on the principle that tissue motion is generally at lower frequencies/velocities than bloodflow as FIG. 2 illustrates, and that the intensity of Doppler signals 112,114 returned from tissue are generally of greater intensity or amplitude than Doppler signals 116,118,120 returned from bloodflow, as FIG. 3 illustrates. These principles are used to shape the response characteristic of the segmentation processor 56, which can appear as shown in FIG. 4. This drawing shows two boundary lines 132 and 134 in the Doppler signal amplitude and velocity/frequency domain. Below boundary line 134 are low amplitude signals which will be generally regarded as noise and not displayed. Above the upper boundary 132 are high amplitude and low frequency Doppler signals which will generally be regarded as tissue signals. Between the two boundaries are lower level, high frequency Doppler signals which will generally be regarded as bloodflow signals.

When an image of only tissue motion is to be displayed, for example, only signals above the upper boundary 132 will be used in the image. When a colorflow image of bloodflow is desired, only signals between the boundaries 132 and 134 will be used. Thus, the segmentation processor 56 separates bloodflow and tissue signals from each other and from noise.

In a preferred embodiment the boundaries 132 and 134 are not fixed, static thresholds but are adaptively determined by other data dependent criteria in addition to Doppler frequency and signal amplitude, such as the presence or absence of grayscale information in the same or adjacent to the image location (pixel) being processed. In this way "fuzzy logic" is used to determine the character of signals that are in the vicinity of the boundaries.

The segmented harmonic bloodflow or tissue signals, or the full bandwidth of both tissue and bloodflow harmonic signals are mapped to a range of color values by a color map 58, which may include scan conversion to the desired image format, if needed. The color map of harmonic Doppler signals may then be overlaid on the grayscale map by a video processor 70. Alternately, the signals of the color map may be blended with the grayscale map values on a pixel by pixel basis. For example, a color pixel may be brightened by the brightness of the corresponding grayscale pixel or the grayscale pixel may be slightly colored in correspondence with the shade of the color pixel, blending the two together.

The color map of moving tissue or of bloodflow may also be displayed alone, if desired. A further alternative is to process a sequence of grayscale or color maps or both three dimensionally by a 3D processor 60. A 3D rendering of harmonic bloodflow alone using the techniques described in U.S. Pat. Nos. 5,474,073 and 5,485,842 may be performed, or a combined 3D image of both harmonic color and grayscale may be formed using the techniques of U.S. Pat. Nos. 5,669,385 and 5,720,291.

It is also possible to overlay or blend a harmonic color map with either a harmonic or a fundamental grayscale image. Received echoes in either the fundamental frequency band or the harmonic frequency band can be submitted to the grayscale processor for processing and display with the harmonic tissue or colorflow information. One way to accomplish this is to interleave grayscale transmit pulses with Doppler transmit pulses, with the grayscale echoes being received in the desired frequency band. Another way is to separate the fundamental and harmonic frequency bands through pulse inversion or parallel or time-multiplexed filtering, then directing the fundamental band signals to the grayscale processor 40 and the harmonic signals to the Doppler processor 50.

Yet another form of processing and display is a harmonic color M-mode display. In this technique ensembles of harmonic Doppler signals are repetitively acquired from the same spatial line location, Doppler processed, and displayed as a function of time. The user can discern changes in motion of bloodflow or tissue over time at the displayed line location. This can also be done in three dimensions by acquiring frames of harmonic Doppler information at the same spatial location and displaying the frames three dimensionally with the 3D processor 60, as described in U.S. patent application Ser. No. 08/858,172.

As mentioned above, there are two preferred techniques for separating the fundamental and harmonic signals and frequency bands. One is the pulse inversion technique, by which two lines are acquired at the same spatial location and differentiated as described in U.S. Pat. No. 5,706,819. The two lines are acquired from transmit waveforms which are of opposite phase. The first line is stored in the line buffer 30, then added to the second line on a spatial basis as the second line is received at adder 32. Since the two received signals are from oppositely phased transmit signals, the fundamental components will be of opposite phase and will cancel. The higher order harmonic components, being quadratic functions, will not cancel but will constructively combine. Thus, the fundamental signals will be eliminated and the harmonic signals reinforced, leaving the harmonic signal components for subsequent harmonic signal processing.

Of course, if the two lines of signals are subtracted rather than added, the fundamental components will reinforce and the harmonic components will cancel, leaving fundamental signals for subsequent processing free of harmonic components.

The second way to separate the fundamental and harmonic bands is by digital filtering. The preferred way to do this in the embodiment of FIG. 1 is to bypass the line buffer 30 so that the full received passband of signals is presented to the QBP 36. The coefficients of the QBP 36 are chosen so that the QBP operates as an FIR or IIR filter which defines the harmonic passband. Thus, the QBP will essentially filter out the fundamental frequency band, leaving the harmonic signal components for subsequent harmonic signal processing and display.

The signals produced by the video processor are displayed on the image display 80.

Harmonic Doppler imaging has been found to be well suited to a number of diagnostic applications. When an echocardiologist is trying to discern the moving endocardium, reverberations from the ribs and echo returns from bloodflow inside the heart chamber would be viewed as clutter. Forming an image from only the harmonic signals from moving tissue by Doppler processing and segmentation of the tissue signals will better enable the echocardiologist to visualize the delicate tissue lining the beating heart. Furthermore, by virtue of the fact that the Doppler processor is processing harmonic signals, the clutter or haze from rib reverberations that is common in fundamental frequency cardiac images is substantially eliminated, Rib reverberations occur in the near field and have very low nonlinear or harmonic artifacts. This is largely due to the fact that nonlinear signal components only begin to arise beyond the near field. Similarly, the clutter due to differing velocities of acoustic travel through fatty tissue beneath the skin is largely eliminated by the use of harmonic Doppler processing. The harmonic tissue signals are sufficiently above customary noise levels in an embodiment of the present invention, even considering depth dependent attenuation, so that deep structures such as the heart wall in the center of the chest cavity can be readily Doppler processed and imaged, which may not be the case with many bloodflow signals. The higher level of the harmonic tissue signals affords a ready means for segmenting the harmonic tissue signals from harmonic bloodflow signals and other low level noise.

Doppler processed harmonic signals exhibit greater resolution than their fundamental frequency counterparts due to the higher frequencies involved. This means that an embodiment of the present invention will exibit better Doppler resolution for the same pulse repetition frequency (PRF) as compared to the same system operated at the fundamental frequency. When the PRF remains constant the effect on the range of Doppler detection is to halve the top end of the velocity range; a fundamental frequency Doppler range having a maximum velocity of 20 cm/sec would become a range topping at 10 cm/sec in harmonic Doppler operation. This lends the system well to harmonic tissue Doppler imaging, where velocities are expectedly lower than in bloodflow applications.

The principles of the present application may also be applied to spectral Doppler. Ensembles of harmonic Doppler signals can be repetitively acquired from the same sample volume and Doppler processed to develop spectral lines representing the instantaneous spectrum of velocities occurring at the sample volume locations. The spectral lines are displayed in a sweeping or scrolling display with time, providing information of the change in bloodflow velocities with the changing effects of the heartbeat cycle.

What is claimed is:

1. A method for imaging moving tissue or bloodflow inside the body comprising:

transmitting a band of ultrasonic signal frequencies into the body including a fundamental frequency $f_{tr}$ at a pulse repetition frequency;

receiving a band of ultrasonic signal frequencies returned in response to said transmitted signal frequencies, including a harmonic of said fundamental frequency developed by the passage of said transmitted signals through the body;

Doppler processing said received harmonic signals using a harmonic reference frequency; and displaying moving tissue or bloodflow information derived from said Doppler processed harmonic signals.

2. The method of claim 1, wherein said received harmonic signals are received from moving tissue, and wherein the step of displaying comprises displaying Doppler processed harmonic tissue signals on a spatial basis.

3. The method of claim 1, further comprising the step of segmenting harmonic tissue signals from harmonic bloodflow signals on a frequency basis.

4. The method of claim 1, further comprising the step of segmenting harmonic tissue signals from harmonic bloodflow signals on an intensity or amplitude basis.

5. The method of claim 1, wherein said step of displaying displays said moving tissue or bloodflow information in three dimensions.

6. The method of claim 1, wherein said step of receiving comprises receiving an ensemble of harmonic signals from the same spatial location; and wherein said step of Doppler processing comprises Doppler processing said ensemble of signals to determine a Doppler shift $\Delta f$ utilizing a reference term $2f_{tr}$.

7. An ultrasonic diagnostic imaging system for imaging moving tissue or bloodflow inside the body comprising:

a probe for transmitting a band of ultrasonic signal frequencies into the body including a fundamental frequency $f_{tr}$ and receiving an ensemble of signals exhibiting a band of ultrasonic signal frequencies including a harmonic frequency developed in response to the passage of said transmitted signal frequencies through the body;

a circuit for separating signals of said harmonic frequency;

a Doppler processor for processing said ensemble of received harmonic signals using a harmonic reference frequency; and a display for displaying moving tissue or bloodflow information derived from said Doppler processed harmonic signals.

8. The ultrasonic diagnostic imaging system of claim 7, further comprising a segmenting circuit for separating harmonic signals emanating from bloodflow from harmonic signals emanating from moving tissue.

9. The ultrasonic diagnostic imaging system of claim 8, wherein said segmenting circuit segments moving tissue signals from bloodflow signals on the basis of frequency.

10. The ultrasonic diagnostic imaging system of claim 8, wherein said segmenting circuit segments moving tissue signals from bloodflow signals on the basis of intensity.

11. The ultrasonic diagnostic imaging system of claim 8, wherein said segmenting circuit utilizes fuzzy logic to distinguish harmonic tissue Doppler signals from harmonic bloodflow Doppler signals.

12. The ultrasonic diagnostic imaging system of claim 7, wherein said circuit for separating signals further comprises a filter for separating a band of frequencies including a harmonic of said fundamental frequency from said received signals.

13. The ultrasonic diagnostic imaging system of claim 12, wherein said filter comprises a programmable digital filter.

14. The ultrasonic diagnostic imaging system of claim 12, wherein said filter comprises a pulse inversion circuit.

15. A method for imaging moving tissue or bloodflow inside the body comprising:
   transmitting a band of ultrasonic signal frequencies into the body including a fundamental frequency $f_{tr}$;
   receiving a band of ultrasonic signal frequencies returned in response to said transmitted signal frequencies, including a harmonic of said fundamental frequency developed by the passage of said transmitted signals through the body;
   separating signals of said harmonic frequency range from signals of said fundamental frequency range;
   grayscale processing at least some of said received signals;
   Doppler processing at least some of said received harmonic signals using a harmonic reference frequency to determine a Doppler shift or velocity;
   forming an image which combines grayscale processed signals with Doppler processed harmonic signals; and
   displaying said image.

16. The method of claim 15, wherein said Doppler harmonic signals are blended with grayscale signals on a spatial basis.

17. The method of claim 15, wherein said image is displayed in three dimensions.

18. An ultrasonic diagnostic imaging system for imaging moving tissue or bloodflow inside the body comprising:
   a probe for transmitting ultrasonic signals exhibiting a fundamental frequency $f_{tr}$ into the body at a pulse repetition frequency and receiving fundamental frequency signals and signals exhibiting a nonlinear component developed in response to the passage of said transmitted signals through the body;
   a circuit for separating nonlinear component signals;
   a Doppler processor for processing said nonlinear component signals over a differently resolved velocity range as compared to that which would be obtained by operating at the fundamental frequency; and
   a display for displaying moving tissue or bloodflow information derived from said Doppler processed nonlinear component signals.

19. The ultrasonic diagnostic imaging system of claim 18, wherein said differently resolved velocity range exhibits a reduced maximum value as compared to that which would be obtained by operating at the fundamental frequency.

20. The ultrasonic diagnostic imaging system of claim 19, wherein said differently resolved velocity range exhibits a maximum value which is half that which would be obtained by operating at the fundamental frequency.

21. The ultrasonic diagnostic imaging system of claim 18, wherein said Doppler processor computes a Doppler shift utilizing a factor $2f_{tr}$ as compared to the use of a factor $2f_{tr}$ when operating at the fundamental frequency.

22. An ultrasonic diagnostic imaging system for imaging moving tissue inside the body comprising:
   a probe for transmitting an ensemble of fundamental frequency signals into the body and receiving fundamental frequency signals and harmonic signals developed in response to the passage of said transmitted signals through the body;
   a circuit for separating said harmonic signals;
   a Doppler processor for processing said harmonic signals to exhibit better Doppler resolution as compared to that which would be obtained by operating at the fundamental frequency; and
   a display for displaying moving tissue information derived from said Doppler processed harmonic signals.

23. The ultrasonic diagnostic imaging system of claim 22, wherein said Doppler processor utilizes a Doppler shift estimator referenced to $2f_{tr}$, where $f_{tr}$ is the fundamental frequency.

24. The ultrasonic diagnostic imaging system of claim 23, wherein said Doppler processor is compared to utilizing a Doppler shift estimator referenced to $f_{tr}$ when operating at the fundamental frequency.

25. An ultrasonic diagnostic imaging system for imaging moving tissue or bloodflow inside the body comprising:
   a probe for transmitting a series of fundamental frequency ($f_{tr}$) signals into the body and receiving an ensemble of harmonic signals developed in response to the passage of said transmitted signals through the body;
   a Doppler processor for processing said ensemble of harmonic signals utilizing a Doppler shift estimator using a harmonic reference frequency; and
   a display for displaying moving tissue or bloodflow information derived from said Doppler processed harmonic signal ensemble.

26. The ultrasonic diagnostic imaging system of claim 25, wherein said display comprises a spectral Doppler display.

27. The ultrasonic diagnostic imaging system of claim 25, wherein said Doppler shift estimator is referenced to $2f_{tr}$.

28. The ultrasonic diagnostic imaging system of claim 25, wherein said Doppler shift estimator estimates velocity.

29. The ultrasonic diagnostic imaging system of claim 28, wherein said display comprises a Doppler velocity display.

30. The ultrasonic diagnostic imaging system of claim 25, further comprising a 3D image processor having an input coupled to said Doppler processor and an output coupled to said display.

31. The ultrasonic diagnostic imaging system of claim 25, further comprising a segmentation processor which distinguishes harmonic tissue Doppler signals from harmonic bloodflow Doppler signals.

32. The ultrasonic diagnostic imaging system of claim 25, further comprising a separating circuit for separating harmonic and fundamental frequency signals.

33. The ultrasonic diagnostic imaging system of claim 32, wherein said separating circuit comprises a digital filter.

34. The ultrasonic diagnostic imaging system of claim 32, wherein said separating circuit operates by combining at least two signals received from the same spatial location.

35. The ultrasonic diagnostic imaging system of claim 34, wherein said separating circuit comprises a pulse inversion processor.

36. The ultrasonic diagnostic imaging system of claim 25, wherein said Doppler shift estimator computes a Doppler shift or velocity utilizing an expression of the form $$\Delta f = \frac{2v f_o \cos \theta}{c}$$

where $f_0 = 2f_{tr}$.

* * * * *